United States Patent [19]

Glass

[11] 4,434,820
[45] Mar. 6, 1984

[54] SYRINGE LOADER AND METHOD

[76] Inventor: John P. Glass, Cava Industries, 79 La Grange Ave., Essington, Pa. 19029

[21] Appl. No.: 374,946

[22] Filed: May 5, 1982

[51] Int. Cl.³ .............................................. B65B 3/12
[52] U.S. Cl. ........................................ 141/2; 141/27; 141/95; 141/375; 141/100; 222/44; 222/309; 604/208; 33/1 V
[58] Field of Search ..................... 141/2, 18, 21–29, 141/100–107, 94, 95, 96, 19, 329, 330, 375; 604/3, 208; 73/864.22, 864.25, 864.87; 222/43, 44, 309; 33/1 V

[56] References Cited

U.S. PATENT DOCUMENTS 3,770,026 11/1973 Isenberg ..................... 141/2
3,875,979 4/1975 Hults ......................... 604/208
4,252,159 2/1981 Maki .......................... 604/208

*Primary Examiner*—Houston S. Bell, Jr.
*Attorney, Agent, or Firm*—John F. A. Earley

[57] ABSTRACT

A syringe loader and method that fill a syringe with a correct dosage of two or more ingredients without referring to or seeing the syringe graduation markings, comprising a bottle holder cradle, a syringe carriage slidably connected to the bottle holder cradle, alignment apparatus for aligning the syringe with each of the bottles and inserting the syringe needle into each bottle, and a dosage gage and a dosage stop indicator for loading the correct dosage from each bottle into the syringe.

11 Claims, 35 Drawing Figures

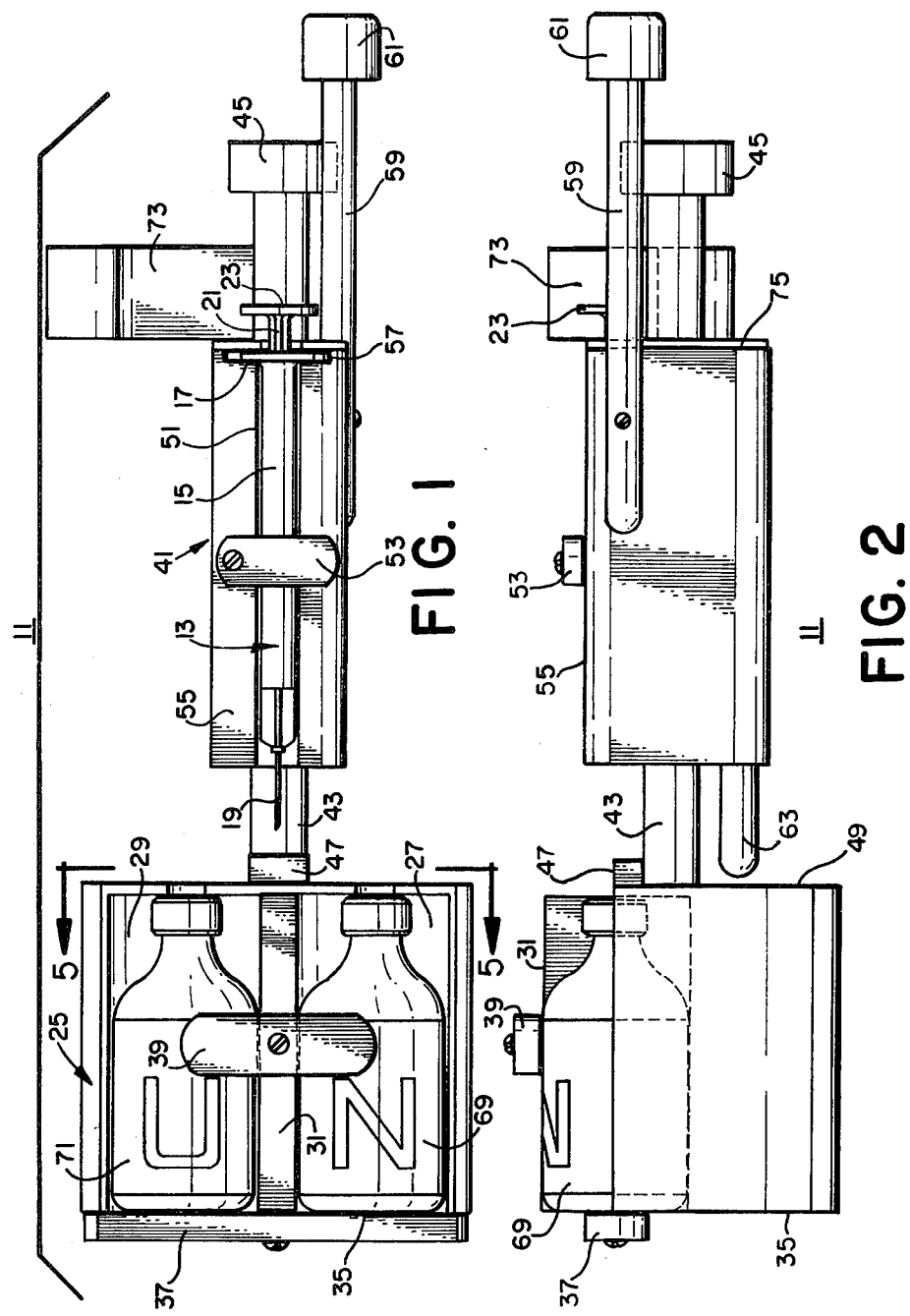

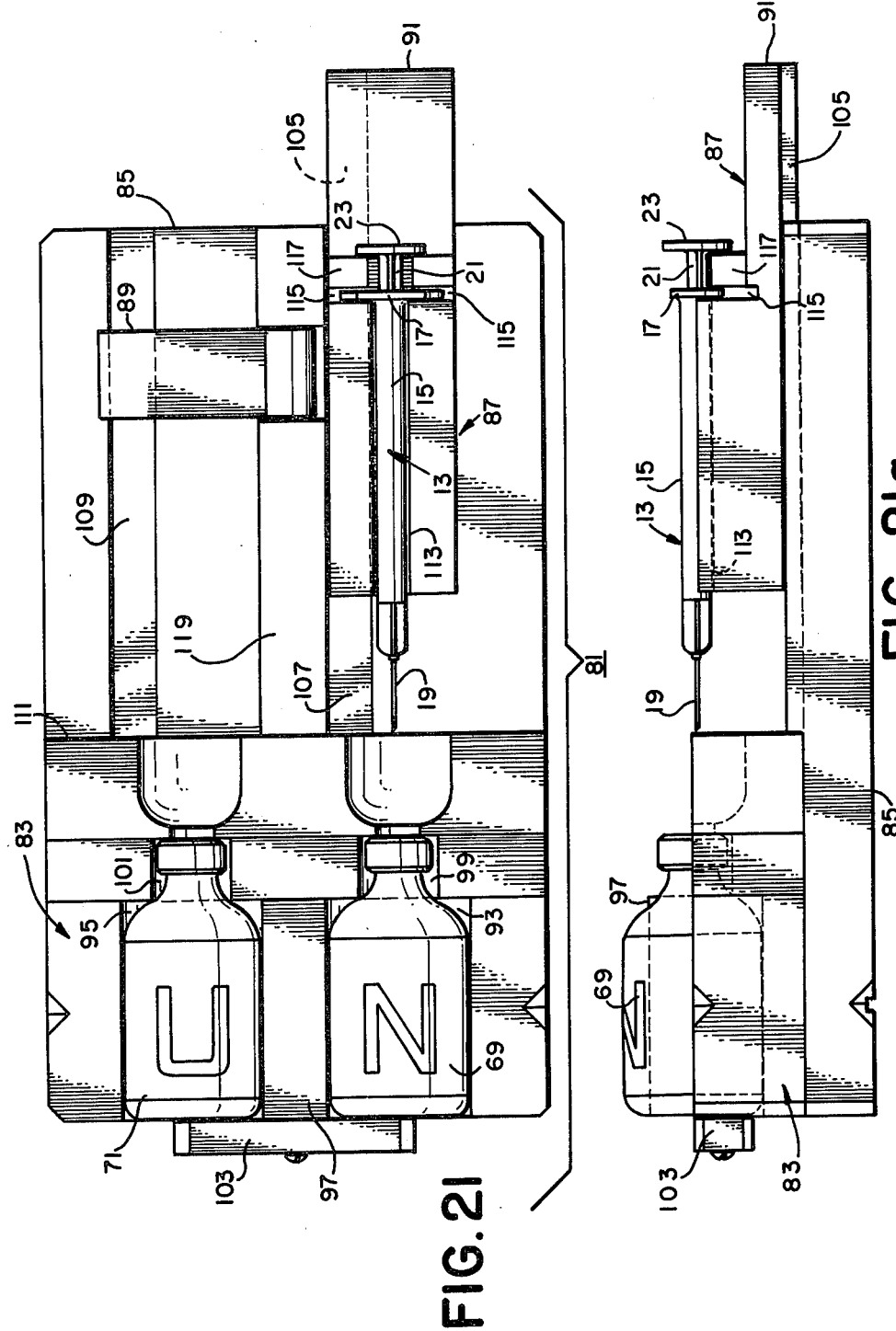

SYRINGE LOADER AND METHOD

BACKGROUND OF THE INVENTION

It has been a problem for persons, who cannot see well enough to read the graduations marked on a syringe or to read the labels of a bottle, to load the syringe with the proper dosage of the ingredients of one or more bottles. For example, in loading a springe with the proper dosage of two bottles for an injection of insulin for the treatment of diabetes, the conventional procedure for a person who can see well is to withdraw the plunger of a syringe to the proper graduation for the required total dosage of the ingredients of two bottles, insert the needle of the syringe into the first bottle and press the syringe plunger forwardly to a selected graduation marked on the syringe to insert an amount of air into the bottle equal to the proper dosage of that bottle's ingredients, withdraw the needle from that bottle, insert the needle into a second bottle and push the plunger forwardly as far as it will go to inject into the second bottle an amount of air equal to the doage desired from the second bottle, withdraw the syringe plunger to the graduation mark on the syringe barrel which loads the syringe with the proper dosage of the ingredients of the second bottle, withdraw the syringe and its needle from the second bottle, insert the needle into the first bottle, and withdraw the plunger to the desired graduation mark on the syringe barrel to load the syringe with the proper dosage of the ingredients of the first bottle, whereby the total dosage of ingredients from the first and second bottle is the correct dosage.

However, if the operator or person loading the syringe cannot see well enough to read the graduation markings on the syringe, he cannot load the syringe with the proper dosage.

SUMMARY OF THE INVENTION

Accordingly, it is an object of this invention to overcome the problems of the prior art faced by persons who cannot see well enough to read the graduations marked on a syringe and so therefore cannot see well enough to load the syringe with the correct dosage of the ingredients of one or more bottles.

In accordance with the present invention, a syringe loader and method are provided that include cradle means for holding one or more bottles, carriage means for holding a syringe, means for inserting the syringe needle into a left-hand bottle and injecting therein an amount of air equal to the required left-hand bottle ingredient dosage without reading the markings on the syringe, means for inserting the syringe needle into a right-hand bottle and injecting therein an amount of air equal to the required right-hand bottle ingredient dosage without reading the graduations marked on the syringe, and for loading the syringe with slightly more right-hand bottle ingredients than required, and for obtaining the correct dosage of the right-hand bottle ingredients by injecting back into the right-hand bottle the overdosage of right-hand bottle ingredients without reading the graduation markings on the syringe, and means for loading the syringe with the correct dosage of left-hand bottle ingredients without reading the graduations marked on the syringe.

BRIEF DESCRIPTION OF THE DRAWINGS

FIG. 1 is a view in top plan of a hand-held syringe loader constructed in accordance with this invention;

FIG. 2 is a view in side elevation of the syringe loader of FIG. 1;

Figure 3:
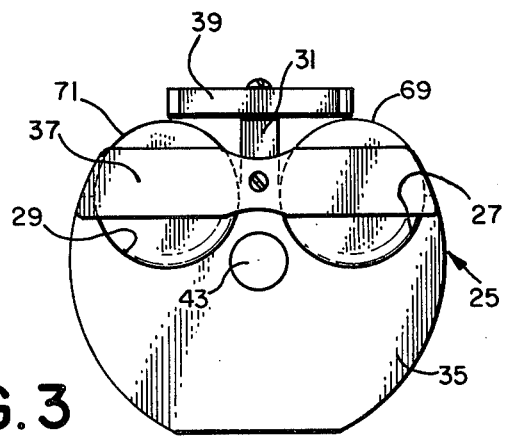
FIG. 3 is a view of the forward end of the syringe loader of FIG. 1.
Figure 4:
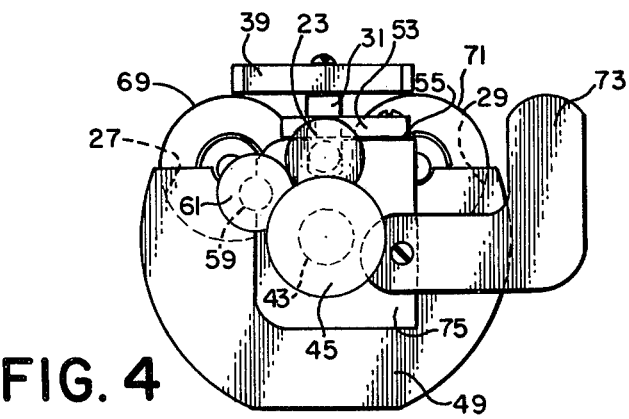
FIG. 4 is a view of the rear end of the syringe loader of FIG. 1.
Figure 5:
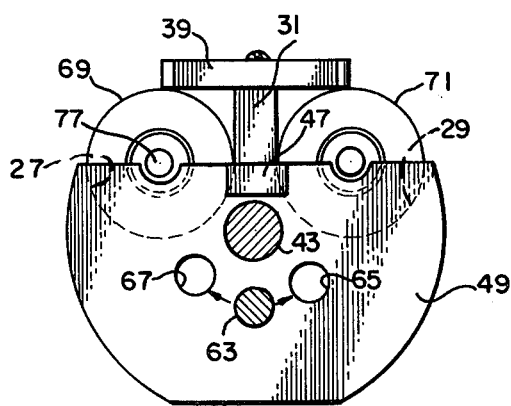
FIG. 5 is a view in section of the syringe loader of FIG. 1 taken as indicated by the lines and arrows 5—5 which appear in FIG. 1.
Figure 21B:
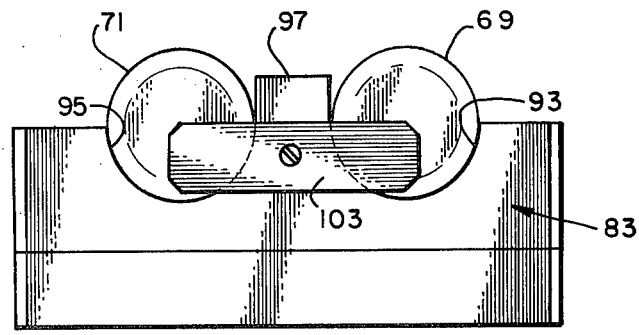
Figure 21C:
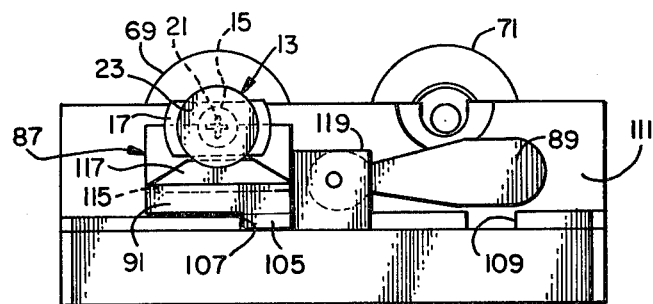
Figure 22:
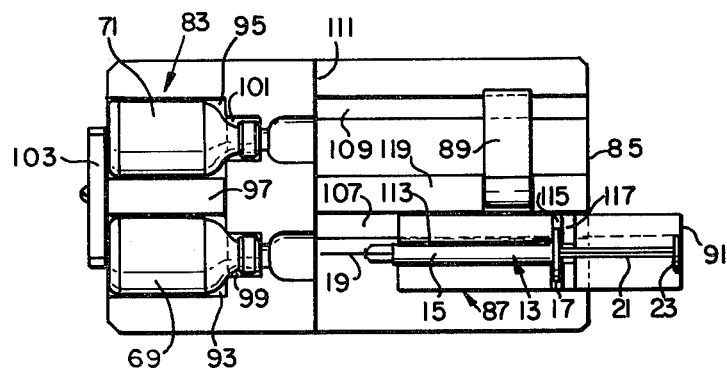
Figure 23:
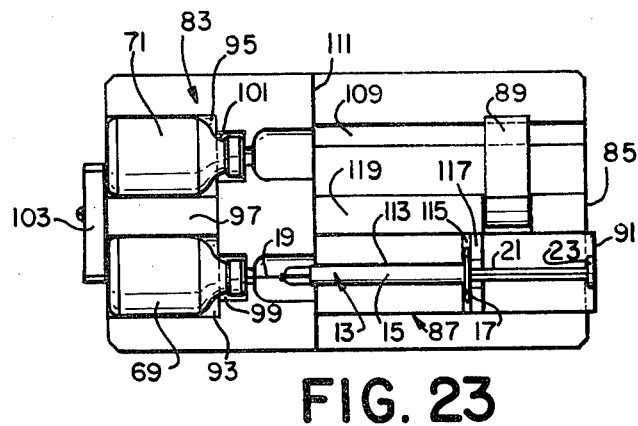
Figure 24:
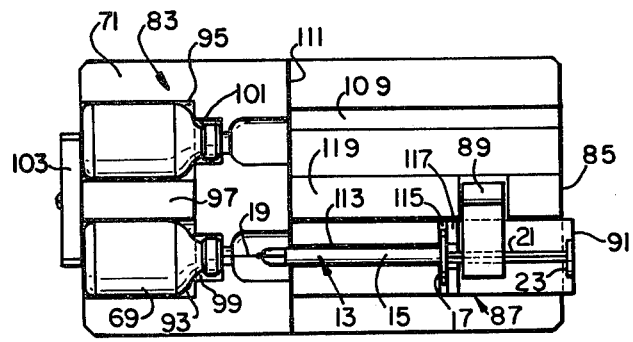
Figure 25:
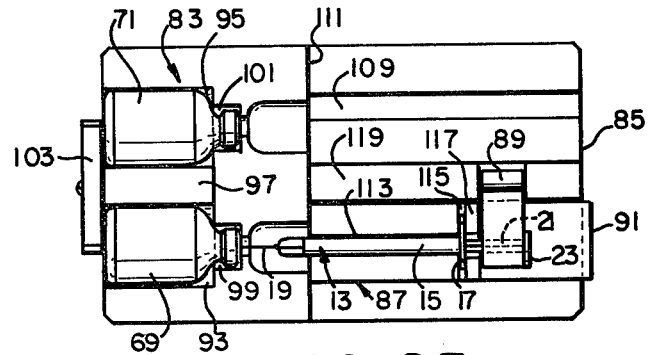
Figure 26:
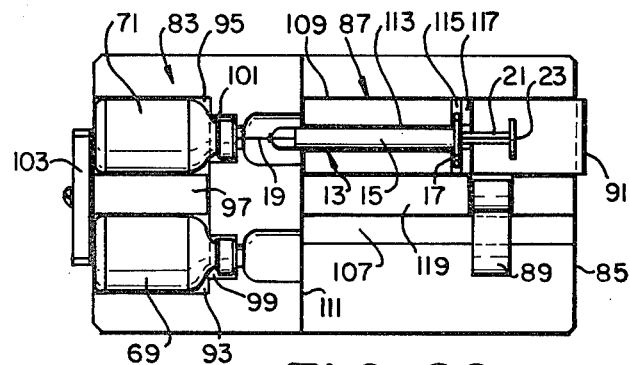
Figure 27:
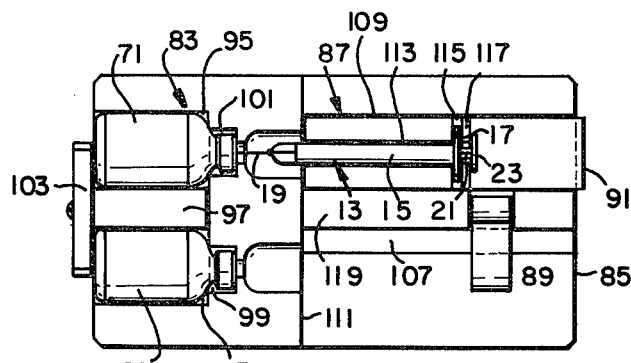
Figure 28:
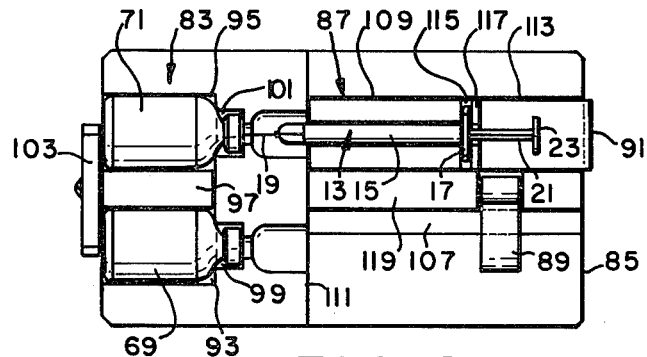
Figure 29:
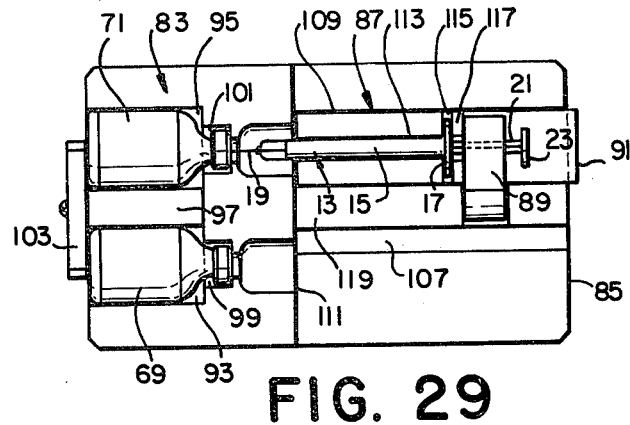
Figure 30:
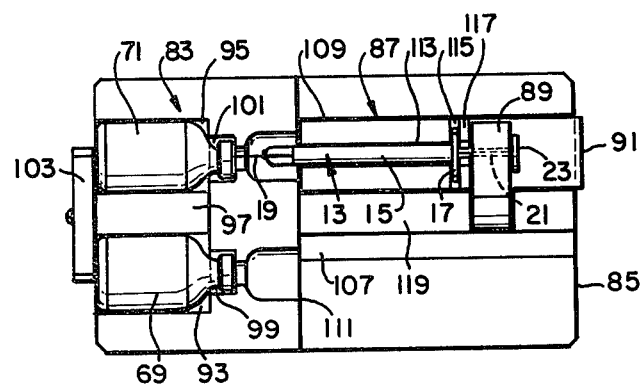
Figure 31:
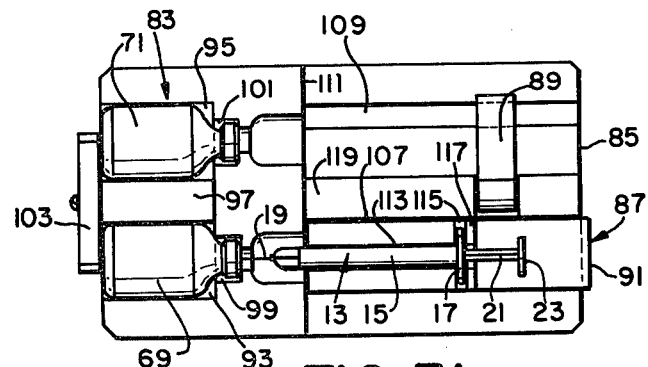
Figure 32:
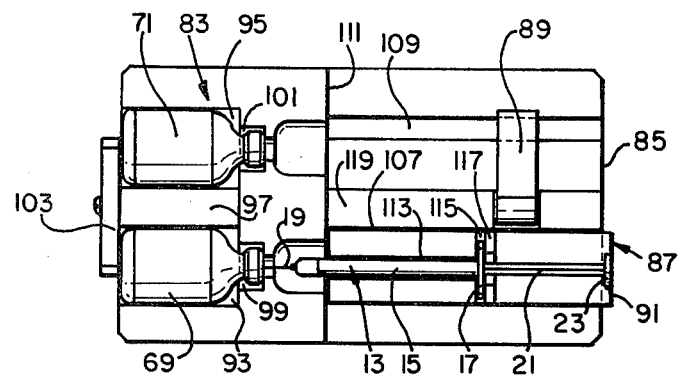

Referring now to the drawings showing the table-top embodiment of the invention;

FIG. 21 is a view in top plan of a table-top syringe loader constructed in accordance with this invention;

FIG. 21a is a view in side elevation of the syringe loader of FIG. 21;

FIG. 21b is a view in elevation of the forward end of the syringe loader of FIG. 21;

FIG. 21c is a view in elevation of the rear end of the syringe loader of FIG. 21;

FIG. 22 is a view in top plan of the syringe loader of FIG. 21 ready to be loaded with correct dosages from the bottles and shows the syringe plunger withdrawn so that its base flange is positioned at a dosage stop indicator which corresponds to the base flange position when the syringe is fully loaded with the correct full dosage;

FIG. 23 shows the next step in the loading process with the syringe carriage in contact with the bottle cradle and the needle inserted into the left-hand bottle;

FIG. 24 shows the next step with the dosage gage rotated into position over the syringe plunger to obstruct the path of the plunger base flange;

FIG. 25 shows the next step with the syringe plunger pressed forwardly until the plunger base flange contacts the dosage gage to thereby inject a correct dosage of air into the left-hand bottle;

FIG. 26 shows the step of inserting the syringe carriage into the alignment slot of the right-hand bottle and inserting the needle into the right-hand bottle;

FIG. 27 shows the step of pressing the syringe plunger forwardly as far as it will go to insert a correct amount of air into the right-hand bottle;

FIG. 28 shows the step of withdrawing the syringe plunger so that its base flange travels past the dosage gage and thereby loads the syringe with an overdose of the ingredients of the right-hand bottle;

FIG. 29 shows the step of rotating the dosage gage into position across the syringe plunger;

FIG. 30 shows the step of obtaining the correct dosage of the ingredients of the right-hand bottle by pushing the plunger forwardly until its base flange contacts the dosage gage;

FIG. 31 shows the step of inserting the needle into the membrane of the left-hand bottle by aligning the carriage with the right-hand cradle seat and inserting the needle into the right-hand bottle; and FIG. 32 shows the step of withdrawing the correct dosage from the left-hand bottle by pulling the plunger rearwardly until its space flange coincides with the dosage stop indicator formed by the rear end of the carriage.

DETAILED DESCRIPTION

Turning now to the drawings, the invention comprises a hand-held syringe loader 11 for loading a correct dosage into a syringe 13 having a barrel 15 with a collar 17 at its rear end, and a needle 19 extending from its forward end. A plunger 21 is positioned inside barrel 15 and has a flanged base or base flange 23 at its rear end.

Syringe loader 11 includes a bottle cradle 25 having a left-hand bottle seat 27 separated from a right-hand bottle seat 29 by a separator 31. The bottle seats 27,29 are open at their tops and at their forward ends 35 to allow for easy insertion therein of the bottles.

A forward bottle retainer 37 is pivotally mounted on the forward end of bltle cradle 25 and is rotated to horizontal position to close the forward end of bottle cradle 25 and prevent the bottle from falling out of the cradle 25 through seat ends 35. The forward end of bottle cradle 25 is opened by rotating retainer 37 to vertical position.

An upper bottle retainer 39 is pivotally mounted on separator 31 and is positioned transversely to separator 31 to close the tops of bottle cradle 25 and prevent the bottles from dropping out. The retainer 39 is positioned parallel to separator 31 to open the tops of bottle cradle 25 in order to place the bottles into the cradle seats 27,29.

A syringe carriage 41 is slidably mounted on a carriage axle 43 that extends from bottle retainer or cradle 25. A carriage stop 45 is mounted on the rear end of carriage axle 43 to limit the rearward movement of the carriage 41, and a needle spacer 47 is mounted on the rear surface or wall 49 of bottle cradle 25 to limit the forward movement of syringe carriage 41.

A syringe groove 51 is formed in the top of the syringe carriage 41 to receive the barrel 15 of syringe 13, and a syringe retainer 53 is pivotally mounted on top 55 of carriage 41 to hold the syringe 13 in the groove 51 when the syringe retainer is positioned transversely of groove 51.

A transverse collar slot 57 is formed in the syringe carriage 41 at the base of syringe groove 51 to receive the collar 17 of syringe barrel 15 and restrict the syringe barrel 15 from moving forwardly and rearwardly.

A dosage stop rod 59 is mounted on and extends rearwardly from syringe carriage 41 and includes a dosage stop 61 which limits the rearward movement of flanged base 23 of plunger 21.

An aligner pin 63 extends forwardly from syringe carriage 41. A right-hand aligner hole 65 and a left-hand aligner hole 67 are formed in the rear surface 49 of bottle cradle 25 and are adapted to receive aligner pin 63 so as to properly position the needle 19 for insertion into left-hand bottle 69 or right-hand bottle 71.

A dosage gage 73 is pivotally mounted on the rear end 75 of carriage 41 and is adapted to be positioned across the syringe plunger 21 when desired to limit the forward movement of syringe plunger 21 by providing a stop for plunger base 23.

In operation, the method of filling syringe 13 with a correct dosage comprises the steps of opening the forward end of bottle cradle 25 by turning forward bottle retainer 37 into a vertical position between the left and right-hand seats 27,29, and opening the top of bottle cradle 25 by turning upper bottle retainer 39 into a position parallel to the separator 31 between the two bottle seats 27,29.

With the bottle seats open, bottle 69 is inserted into left-hand seat 27 and bottle 71 is inserted into right-hand seat 29. Then the forward end of the bottle cradle is closed by turning bottle retainer 37 into horizontal position in contact with the bottom of the bottles, and the top of bottle cradle 25 is closed by turning bottle retainer 39 into a position transverse to separator 31 and in contact with the side wall of the bottles.

Then syringe 13 is placed in syringe groove 51 in the syringe carriage 41 and the syringe barrel collar 17 is seated in collar slot 57 to prevent movement of syringe 13 forwardly or rearwardly.

The syringe 13 is held in groove 51 by rotating the retainer 53 into a position across the top of syringe 13 and the groove 51.

Figure 6:
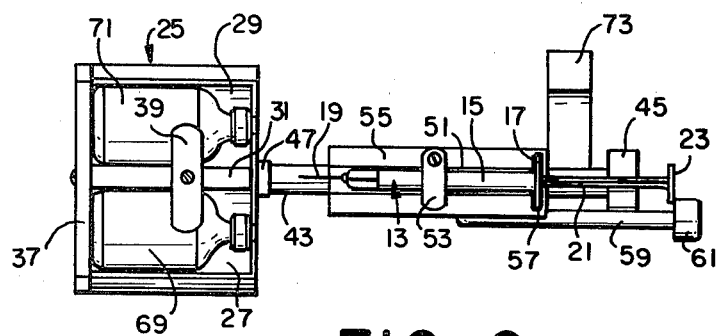
FIG. 6 is a view of the syringe loader of FIG. 1 ready to be loaded with a correct dosage, with the bottles inserted in a bottle cradle and held in place by forward and upper retainers, with the syringe placed in syringe carriage and held in place by a syringe retainer, and with the syringe plunger pulled back so that its flanged base is in contact with a dosage stop.

The syringe is filled with an amount of air equal to the desired total dosage by pulling back the syringe plunger 21 so that the syringe flanged base 23 contacts the dosage stop 61, as shown in FIG. 6.

Figure 7:
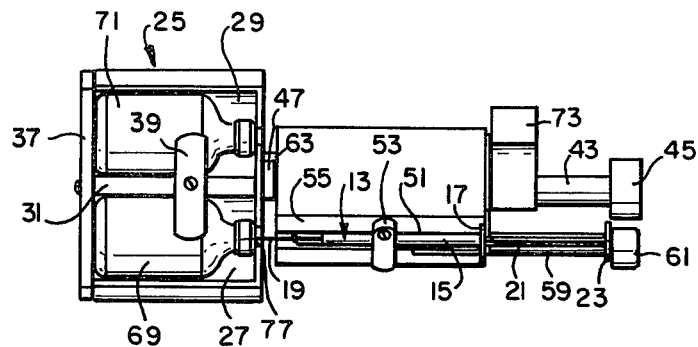
FIG. 7 is a view in top plan of the next loading step with the syringe carriage in contact with the bottle cradle and with a carriage alignment pin seated in a cradle aligner hole and the syringe needle inserted into the bottle through the membrane in the top of the left-hand bottle.

The syringe needle 19 is inserted into the left-hand bottle 69 by turning the syringe carriage 41 counterclockwise while holding the bottle cradle 25 with the forward end 35 facing away from your body, if you are right-handed. Then the syringe carriage 41 is moved forwardly with the right hand into contact with needle spacer 47 mounted on the bottle cradle 25, as shown in FIG. 7. This movement of the carriage 14 also inserts carriage aligner pin 63 into the right-hand aligner hole 65 of bottle cradle 25 and inserts needle 19 into left-hand bottle 69 through membrane 77.

Figure 8:
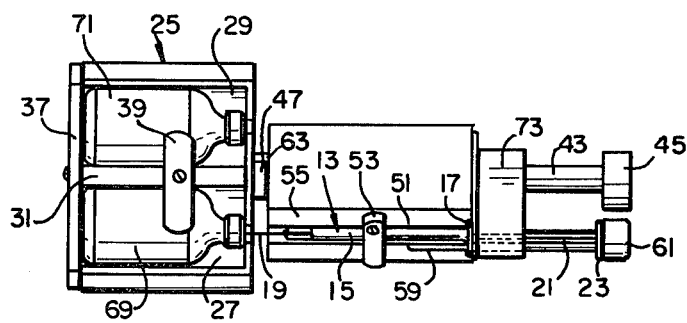
FIG. 8 shows the next step in loading the syringe loader, with the dosage gage placed over the syringe plunger.

The dosage gage 73 is rotated across the syringe plunger 21 (FIG. 8).

Figure 9:
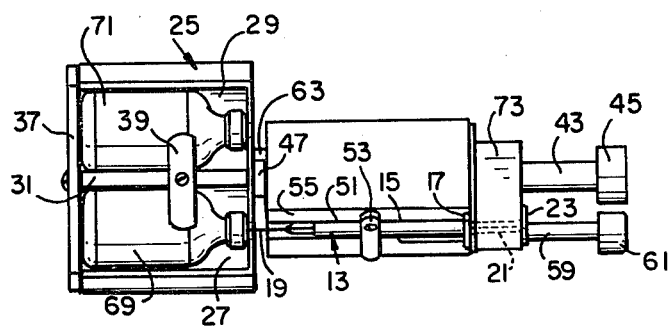
FIG. 9 shows the next step with the syringe plunger pressed forwardly until the plunger base contacts the dosage gage to thereby inject a correct dosage of air into the left-hand bottle.

An amount of air equal to the required left-hand bottle ingredient dosage is injected into the left-hand bottle 69 by pushing the syringe plunger 21 forwardly to bring the bottom flange 23 into contact with the dosage gage 73 (FIG. 9).

Figure 10:
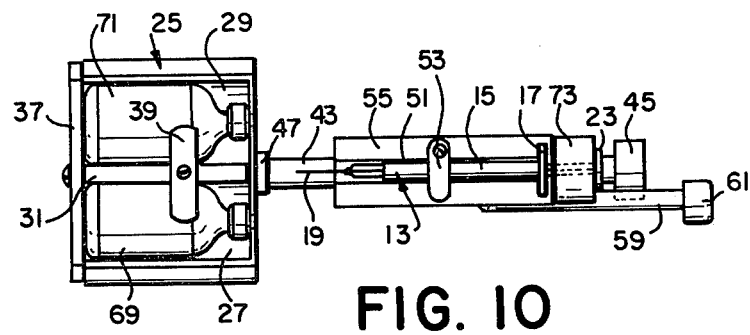
FIG. 10 shows the next step of moving the carriage away from the bottle cradle and thereby withdrawing the needle from the left-hand bottle.

The syringe needle 19 is withdrawn from the left-hand bottle 69 by pulling the carriage 41 away from bottle contact with the cradle 25 (FIG. 10).

Figure 11:
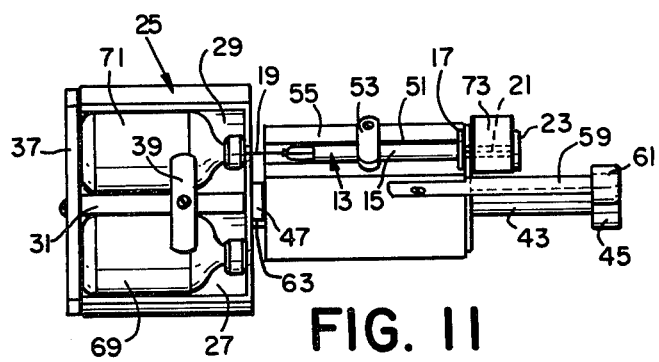
FIG. 11 shows the next step of moving the carriage into contact with the bottle cradle and thereby inserting the needle into the right-hand bottle.

The needle 19 is then inserted into the right-hand bottle 71 by turning the carriage 41 clockwise and moving it forwardly into contact with the bottle cradle needle spacer 47 (FIG. 11). This movement also inserts the carriage aligner pin 63 into the left-hand aligner hole 67 of bottle cradle 25.

Figure 12:
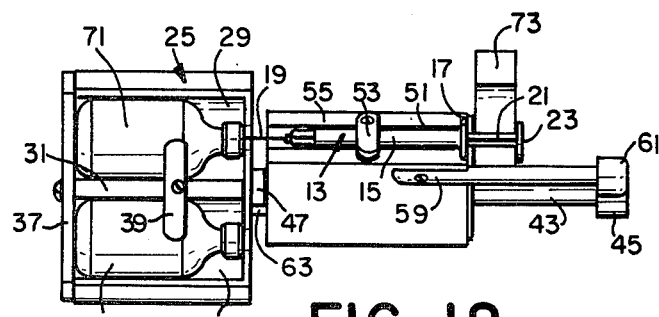
FIG. 12 shows the next step of turning the dosage gage away from its position overlying the syringe plunger.

The syringe plunger 21 is freed to move forwardly by removing the dosage gage 73 from across the plunger 21 and this is done by rotating the dosage gage 73 in a clockwise direction (FIG. 12).

Figure 13:
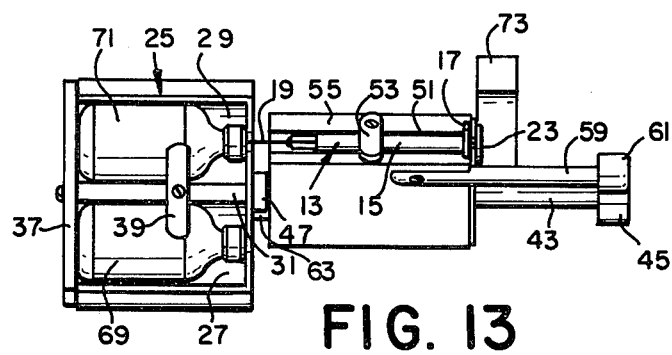
FIG. 13 shows the next step of pressing the syringe plunger forwardly as far as it will go to insert a correct amount of air into the right-hand bottle.

An amount of air equal to the required dosage of the right-hand bottle ingredients is injected into the right-hand bottle 71 by pushing the plunger 21 forwardly as far as it will go (FIG. 13).

Figure 14:
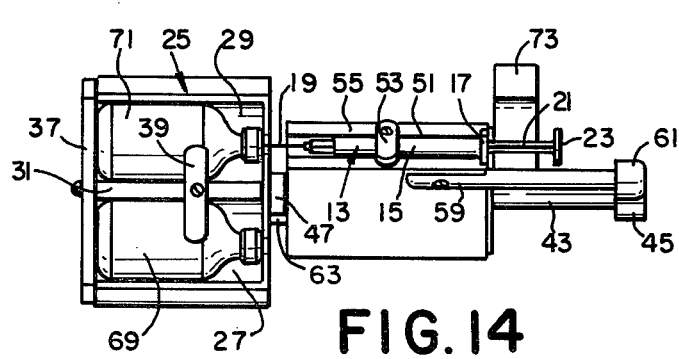
FIG. 14 shows the next step of withdrawing the syringe plunger so that its base travels past the dosage gage and thereby loads the syringe with an overdose of the ingredients of the right-hand bottle.
Figure 15:
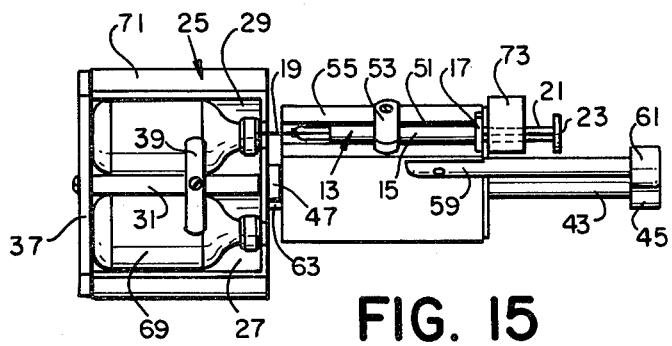
FIG. 15 shows the next step of rotating the dosage gage into position across the syringe plunger.
Figure 16:
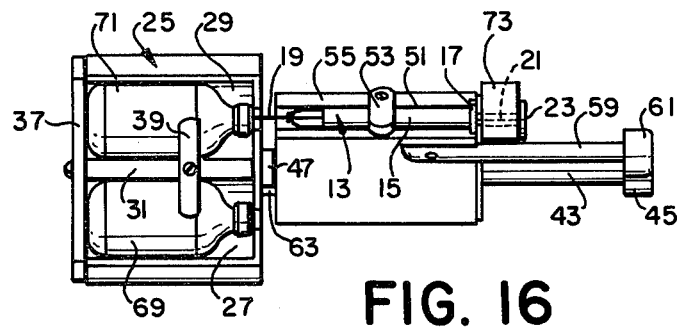
FIG. 16 shows the next step of obtaining the correct dosage of the ingredients of the right-hand bottle by pushing the plunger forwardly until its base contacts the dosage gage.
Figure 17:
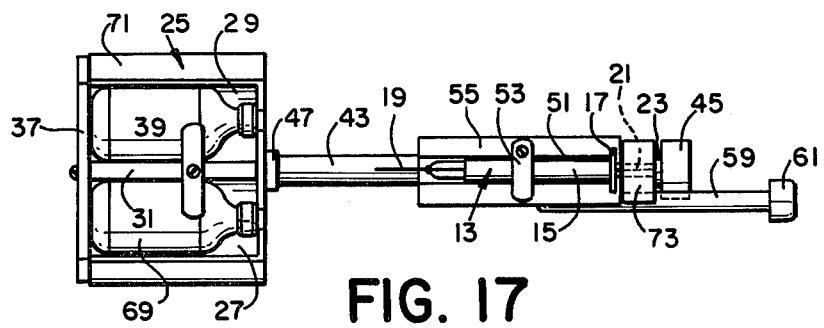
FIG. 17 shows the next step of withdrawing the needle from the right-hand bottle by pulling the carriage away from the cradle until the carriage makes contact with the carriage stop.

Then the syringe 13 is loaded, with slightly more right-hand bottle ingredients than required, by holding the carriage 41 against the cradle 25 and pulling back the plunger 21 until its bottom flange 23 just clears the dosage gage 73 (FIG. 14). The dosage gage 73 is moved over the plunger 21 by rotating the dosage gage counterclockwise (FIG. 15), and the correct dosage of right-hand bottle ingredients is obtained by injecting back into the right-hand bottle 71 the overdosage amount of right-hand bottle ingredients by pushing plunger 21 forwardly so that its bottom flanged base 23 contacts the dosage gage 73 (FIG. 16). The needle 19 is withdrawn from the right-hand bottle 71 by pulling the carriage 41 away from the bottle cradle 25 (FIG. 17).

Figure 18:
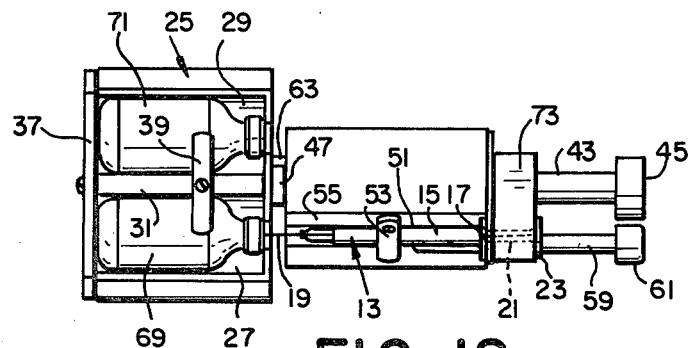
FIG. 18 shows the next step of inserting the needle into the membrane of the left-hand bottle by aligning the carriage alignment pin with the right-hand cradle aligner hole, and by pushing the carriage forwardly as far as it will go.

The needle 19 is inserted into the left-hand bottle 69 by turning the carriage 41 counterclockwise and moving the carriage 41 forwardly into contact with needle spacer 47 (FIG. 18). This movement inserts syringe carriage aligner pin 63 into the right-hand aligner hole 65 of the bottle cradle 25.

Figure 19:
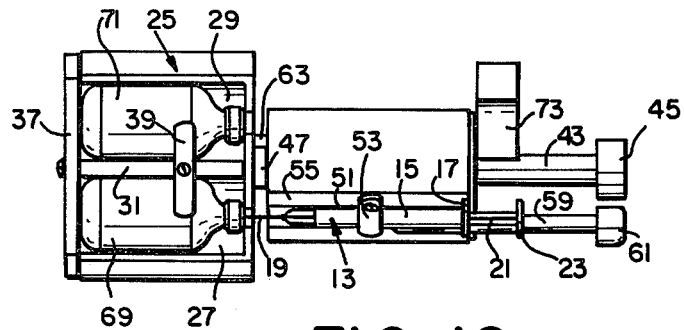
FIG. 19 shows the next step of rotating the dosage gage away from its position overlying the syringe plunger.
Figure 20:
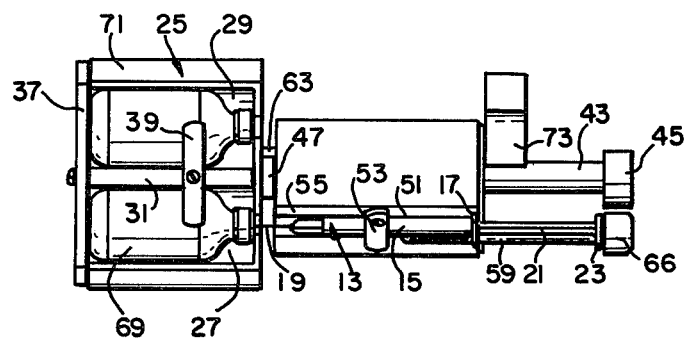
FIG. 20 shows the next step of withdrawing the correct dosage from left-hand bottle by pulling the plunger rearwardly until the syringe plunger flanged base contacts the dosage stop.

The dosage gage 73 is removed from across the plunger 21 by rotating the dosage gage 73 counterclockwise (FIG. 19), and the syringe 13 is loaded with the correct dosage of left-hand bottle ingredients by holding the syringe carriage 41 in place and pulling the plunger 21 into contact with the dosage stop 61 (FIG. 20).

The needle is removed from the left-hand bottle 69 by pulling the syringe carriage 41 to the carriage stop 45.

By following these method steps, the syringe 13 is loaded with the proper dosages of left-hand and right-hand bottle ingredients.

The syringe 13 is freed from the carriage 41 by moving the syringe retainer 53 from across the syringe barrel 15, and carefully removing syringe 13 from groove 51 without changing the setting of the plunger 21 or touching the needle 19.

The syringe 13 is ready for injecting the correct dosage.

Turning now to the table-top syringe loader 81 shown in FIGS. 21 through 32, the syringe loader 81 comprises a bottle cradle 83 mounted on a base 85, a syringe carrier 87 slidably mounted in base 85, a dosage gage 89 rotatably mounted on base 85, and a dosage stop indicator 91 formed by the rear end of syringe carrier 87.

Bottle cradle 83 is provided with a left-hand bottle seat 93 and a right-hand bottle seat 95 with a separator 97 between them. The rear end 99 of left-hand bottle seat 93 is necked-down to accommodate the neck of a bottle 69 and the rear end 101 of bottle seat 95 is similarly necked down to accommodate the neck of a bottle 71.

A retainer 103 is provided at the front end of the bottle seats and is rotated into horizontal position to prevent the bottles from falling out of their seats through the front end of those seats. When it is desired to remove the bottles from their seats, retainer 103 is rotated about its pin to a vertical position. A top retainer is not required, because syringe loader 81 is a table-top embodiment and the bottles remain seated because of the force of gravity.

Syringe carrier 87 is slidably mounted in base 85 because the bottom of syringe carrier 87 has depending therefrom a foot 105 that is adapted to slide in left-hand alignment groove or slot 107 and right-hand alignment groove or slot 109 formed in the base 85.

Rear end wall 111 of cradle 83 provides a forward stop for the syringe carrier 87.

A syringe groove 113 is formed in the top of syringe carriage 87 for receiving the barrel 15 of a syringe 13, and a transverse slot 115 is formed in the top of syringe carriage 87 for receiving the collar 17 of the syringe barrel 15 to prevent the syringe 13 from moving forwardly or rearwardly in the carriage groove 113.

A stop 117 on the carriage 87 forms the rear wall of slot 115 and also forms the forward stop for flanged base 23 of the syringe 13.

Dosage gage 89 is rotatably mounted on a central separator 119 between left-hand alignment slot 107 and right-hand alignment slot 109. Dosage gage 89 is adapted to be positioned across the syringe plunger 21 when it is desired to limit the forward movement of the syringe plunger.

The method of loading the syringe 13 in the table-mounted syringe loader 81 with correct dosages of ingredients comprises the steps of mounting a left-hand bottle 69 into bottle seat 93, and mounting a right-hand bottle 71 in bottle seat 95 with the necks of the bottles pointing rearwardly and seated in the rear ends 99 and 101 of the bottle seats. Retainer 103 is rotated onto horizontal position to contact the bottom of the bottles and hold them from falling out of the forward ends of the bottle seats.

Syringe 13 is placed into groove 113 of carriage 87, its collar 17 seated in carriage transverse slot 115.

Syringe plunger 21 is pulled rearwardly until it coincides with dosage stop indicator 91 (FIG. 22) and carriage 87 is pushed forwardly into contact with cradle rear-end wall 11 so that the needle is inserted into bottle 69 (FIG. 23).

Dosage gage 89 is moved into position over plunger 21 (FIG. 24) and an amount of air equal to the required left-hand bottle ingredient dosage is injected into the left-hand bottle 69 by pushing the base flange 23 into contact with dosage gage 89 (FIG. 25).

Dosage gage 89 is rotated out of the way, and the needle 19 is withdrawn from left-hand bottle 69 by moving the carriage 87 rearwardly out of left-hand alignment groove or slot 107.

Then the carriage 87 is placed in the right-hand alignment slot 109 and is moved forwardly into abutment with rear wall 111 of cradle 83 with the needle 19 inserted into the right-hand bottle 71, as shown in FIG. 26.

An amount of air equal to the required right-hand bottle ingredient dosage is injected into the right-hand bottle 71 by pushing the syringe plunger 21 as far forwardly as it goes (FIG. 27).

Then the syringe 13 is loaded with a slight overdosage of right-hand bottle ingredients by pulling the syringe plunger base rearwardly past the dosage gage 89 (FIG. 28). Then the dosage gage 89 is rotated across the path of the plunger base 23 (FIG. 29), and the correct dosage of right-hand bottle ingredients is obtained by pushing the plunger base 23 against the dosage gage 89 (FIG. 30).

The needle is withdrawn from the right-hand bottle 71 by moving syringe carriage 87 rearwardly away from bottle holder 83 and out of left-hand alignment slot 109. Then the carriage 87 is placed in left-hand alignment slot 107 and moved into abutment with rear wall 111 so that the needle 19 is once again inserted into left-hand bottle 69 (FIG. 31). The correct dosage of right-hand bottle ingredients is obtained by moving the syringe plunger base 23 rearwardly until it coincides with the dosage stop indicator 91 formed by the rear wall of carriage 87 (FIG. 32).

The needle is removed from the left-hand bottle 69 by moving the carriage 87 and cradle 83 apart, whereby the syringe 13 has been loaded with the proper dosages of left and right-hand bottle ingredients.

ADVANTAGES

The syringe loaders of the present invention solve the problem of the prior art presented to those who cannot see well enough to recognize the markings on a syringe by providing a solution to that problem which comprises a method and apparatus for loading the correct dosages into a syringe without referring to or being able to see the markings on the syringe. The method and apparatus are simple and accurate and free the user from improper dosages.

I claim:

1. A syringe loader for loading a correct dosage into a syringe having a barrel with a collar at its rear end and a needle extending from its forward end and a plunger inside the barrel with a flanged base at the rear end of the plunger, comprising cradle means for holding a right-hand bottle and a left hand bottle, carriage means for holding a syringe, means for inserting the syringe needle into the left-hand bottle and injecting therein an amount of air equal to the required left-hand bottle ingredient dosage, means for inserting the syringe needle into the right-hand bottle and injecting therein an amount of air equal to the required right-hand bottle ingredient dosage, means for loading the syringe with slightly more right-hand bottle ingredients than required, means for obtaining the correct dosage of right-hand bottle ingredients by injecting back into the right-hand bottle the overdosage of right-hand bottle ingredients, and means for loading the syringe with the correct dosage of left-hand bottle ingredients.

2. The syringe loader of claim 1, said cradle means including a bottle cradle having a left-hand bottle seat separated from a right-hand bottle seat by a separator, said bottle seats being open at the top and at the forward end, a forward bottle retainer pivotally mounted on the forward end of the bottle cradle to close the forward end of the bottle cradle, when said forward retainer is positioned horizontally, and to open the forward end of the bottle cradle when said forward retainer is positioned vertically, and an upper bottle retainer pivotally mounted on the separator to close the top of the bottle cradle, when said upper retainer is positioned parallel to the separator, and to open the top of the bottle cradle when said upper retainer is positioned transversely to the separator.

3. The syringe loader of claim 1, said carriage means including a syringe carriage slidably mounted on a carriage axle extending from the bottle cradle, a carriage stop mounted on the rear end of the carriage axle to limit the rearward movement of the carriage, a needle spacer mounted on the rear of the bottle cradle to limit the forward movement of the syringe carriage, a syringe groove formed in the top of the syringe carriage for receiving the barrel of the syringe, a syringe retainer pivotally mounted on top of the carriage to hold the syringe in the groove when the syringe retainer is positioned transversely across the groove, and a transverse collar slot formed in the syringe carriage at the rear of the syringe groove for receiving the collar of the syringe barrel.

4. The syringe loader of claim 1, including alignment means between said cradle means and said carriage means for aligning the syringe needle with each bottle.

5. A syringe loader for loading a correct dosage into a syringe having a barrel with a collar at its rear end and a needle extending from its forward end and a plunger inside the barrel with a flanged base at the rear end of the plunger, comprising a bottle cradle having a left-hand bottle seat separated from a right-hand bottle seat by a separator, said bottle seats being open at the top and at the forward end, a forward bottle retainer pivotally mounted on the forward end of the bottle cradle to close the forward end of the bottle cradle, when said forward retainer is positioned horizontally, and to open the forward end of the bottle cradle when said forward retainer is positioned vertically, an upper bottle retainer pivotally mounted on the separator to close the top of the bottle cradle, when said upper retainer is positioned parallel to the separator, and to open the top of the bottle cradle when said upper retainer is positioned transversely to the separator, a syringe carriage slidably mounted on a carriage axle extending from the bottle cradle, a carriage stop mounted on the rear end of the carriage axle to limit the rearward movement of the carriage, a needle spacer mounted on the rear of the bottle cradle to limit the forward movement of the syringe carriage, a syringe groove formed in the top of the syringe carriage for receiving the barrel of the syringe, a syringe retainer pivotally mounted on top of the carriage to hold the syringe in the groove when the syringe retainer is positioned transversely across the groove, a transverse collar slot formed in the syringe carriage at the rear of the syringe groove for receiving the collar of the syringe barrel, a dosage stop connected to and positioned to the rear of the syringe carriage, an aligner pin extending forwardly from the syringe carriage, a right-hand aligner hole and a left-hand aligner hole formed in the base of the bottle cradle, and a dosage gage pivotally mounted on the syringe carriage and adapted to be positioned across the syringe plunger when desired to limit the forward movement of the syringe plunger.

6. The syringe loader of claim 1, said cradle means including a bottle cradle mounted on a base having a left-hand bottle seat separated from a right-hand bottle seat by a separator, said bottle seats being open at the top and the forward end, and a forward bottle retainer pivotally mounted on the forward end of the bottle cradle to close the forward end of the bottle cradle, when said forward retainer is positioned horizontally, and to open the forward end of the bottle cradle when said forward retainer is positioned vertically.

7. The syringe loader of claim 1, said carriage means including a syringe carriage slidably mounted on the base, the rear end of the bottle cradle providing a forward stop for the syringe carriage, a syringe groove formed in the top of the syringe carriage for receiving the barrel of the syringe, and a transverse collar slot formed in the syringe carriage at the rear of the syringe groove for receiving the collar of the syringe barrel.

8. A syringe loader for loading a correct dosage into a syringe having a barrel with a collar at its rear end and a needle extending from its forward end and a plunger inside the barrel with a flanged base at the rear end of the plunger, comprising a bottle cradle mounted on a base having a left-hand bottle seat separated from a right-hand bottle seat by a separator, said bottle seats being open at the top and the forward end, a forward bottle retainer pivotally mounted on the forward end of the bottle cradle to close the forward end of the bottle cradle, when said forward retainer is positioned horizontally, and to open the forward end of the bottle cradle when said forward retainer is positioned vertically, a syringe carriage slidably mounted on the base, the rear end of the bottle cradle providing a forward stop for the syringe carriage, a syringe groove formed in the top of the syringe carriage for receiving the barrel of the syringe, a transverse collar slot formed in the syringe carriage at the rear of the syringe groove for receiving the collar of the syringe barrel, a dosage gage pivotally mounted on the base and adapted to be positioned across the syringe plunger when desired to limit the forward movement of the syringe plunger, and a dosage stop indicator for indicating when the syringe contains a full dosage.

9. A method of loading a syringe with a correct dosage, comprising mounting a left-hand bottle and a right-hand bottle in a bottle cradle of a syringe loader, mounting a syringe in a groove in a syringe carrier of the syringe loader, filling the syringe with an amount of air equal to a desired total dosage without reading any graduation markings on the syringe by pulling the syringe plunger back to a dosage stop indicator affixed to the syringe loader, inserting the syringe needle into the left-hand bottle by aligning the bottle cradle and syringe holder and moving them together, injecting into the left-hand bottle an amount of air equal to the required left-hand bottle ingredient dosage by pushing the base of the syringe plunger into contact with a removable dosage gage mounted in the path of the plunger base, withdrawing the needle from the left-hand bottle by moving apart the bottle cradle and syringe carrier, inserting the syringe needle into the right-hand bottle by aligning the bottle cradle and syringe carrier and moving them together, injecting into the right-hand bottle an amount of air equal to the required right-hand bottle ingredient dosage by removing the dosage gage and by pushing the syringe plunger as far forwardly as it goes, loading the syringe with a slight overdosage of right-hand bottle ingredients by pulling the syringe plunger base back past the dosage gage, obtaining the correct dosage of right-hand bottle ingredients by moving the dosage gage into the path of the plunger base and pushing the plunger base against the dosage gage, withdrawing the needle from the right-hand bottle by moving apart the bottle cradle and syringe carriage, inserting the syringe needle into the left-hand bottle by aligning the bottle cradle and syringe carrier and moving them together, and loading the syringe with the correct dosage of left-hand bottle ingredients by pulling the syringe plunger base back to the dosage stop indicator.

10. A method of loading a syringe with a correct dosage, comprising opening the forward end of a bottle cradle by turning a forward bottle retainer into vertical position on a bottle cradle having left and right-hand seats for two bottles, opening the top of a bottle cradle by turning an upper bottle retainer into a position parallel to a separator between the two bottle seats, inserting a bottle into the left-hand seat and inserting another bottle into the right-hand seat, closing the forward end of the bottle cradle by turning the forward bottle retainer into horizontal position in contact with the bottom of the bottles, closing the top of the bottle cradle by turning the upper bottle retainer transversely into contact with the side wall of the bottles, taking a syringe having a barrel with a collar at its rear end and a needle extending from its front end and having a plunger inside the barrel with a flange at the rear end of the plunger, placing the syringe in a syringe groove in a syringe carriage and seating the syringe barrel collar in a collar slot in the syringe carriage, holding the syringe in the groove by rotating a syringe retainer across the top of the groove, filling the syringe with an amount of air equal to a desired total dosage by pulling the syringe plunger back to contact the dosage stop, inserting the syringe needle into the left-hand bottle by turning the syringe carriage counterclockwise and moving the carriage forwardly as far as it will go into contact with a needle spacer mounted on the bottom cradle and inserting a carriage aligner pin in a right-hand aligner hole of the bottle cradle, rotating the dosage gage across the syringe plunger, injecting into the left-hand bottle an amount of air equal to the required left-hand bottle ingredient dosage by pushing the syringe plunger forwardly to bring the bottom flange of the syringe plunger into contact with the dosage gage, withdrawing the syringe needle from the left-hand bottle by pulling the carriage back into contact with the carriage stop, inserting the needle into the right-hand bottle by turning the carriage clockwise and moving it forwardly as far as it will go into contact with the bottle cradle needle spacer and inserting the carriage aligner pin into the left-hand aligner hole of the bottle cradle, freeing the syringe plunger to move forwardly by removing the dosage gage from across the plunger by rotating the dosage gage clockwise, injecting into the right-hand bottle an amount of air equal to the required dosage of right-hand bottle ingredients by pushing the plunger forwardly as far as it will go, loading the syringe with slightly more right-hand bottle ingredients than required by holding the carriage against the cradle and pulling the plunger back so that its bottom flange clears the dosage gage, moving the dosage gage across the plunger by rotating it counterclockwise, obtaining the correct dosage of right-hand bottle ingredients by injecting back into the right-hand bottle the overdosage amount of right-hand bottle ingredients by pushing the plunger forwardly so that its bottom flange contacts the dosage gage, withdrawing the needle from the right-hand bottle by pulling the carriage back away from the bottle cradle until the carriage contacts the carriage stop, inserting the needle into the left-hand bottle by turning the carriage counterclockwise and moving the carriage forwardly as far as it will go into contact with the needle spacer and inserting the syringe carrier aligner pin in the right-hand aligner hole of the bottle cradle, removing the dosage gage from across the plunger by rotating the dosage gage clockwise, loading the syringe with the correct dosage of left-hand bottle ingredients by holding the syringe carriage in place and pulling the plunger back into contact with the dosage stop, removing the needle from the left-hand bottle by pulling the syringe carriage back to the carriage stop, whereby the syringe has been loaded with the proper dosages of left and right-hand bottle ingredients, freeing the syringe from the carriage by moving the syringe retainer from across the syringe barrel, and carefully removing the syringe from the carriage without changing the setting of the plunger or touching the needle, whereby the syringe is ready for injecting the correct dosage.

11. A method of loading a syringe with a correct dosage, comprising mounting a bottle in the left-hand seat of a bottle cradle, mounting another bottle in the right-hand seat of a bottle cradle, taking a syringe having a barrel with a collar at its rear end and a needle extending from its front end and having a plunger inside the barrel with a flange at the rear end of the plunger, placing the syringe in a syringe groove in a syringe carriage and seating the syringe collar in a collar slot in the syringe carriage, filling the syringe with an amount of air equal to a desired total dosage by pulling the syringe plunger back to a dosage stop indicator, inserting the syringe needle into the left-hand bottle by placing the syringe carriage into a left-hand alignment slot and moving the carriage and cradle together, rotating a dosage gage across the syringe plunger, injecting into the left-hand bottle an amount of air equal to the required left-hand bottle ingredient dosage by pushing the syringe plunger forwardly to bring the bottom flange of the syringe plunger into contact with the dosage gage, withdrawing the syringe needle from the left-hand bottle by moving the carriage away from the cradle, inserting the needle into the right-hand bottle by placing the syringe carriage in a right-hand alignment slot and moving the carriage and cradle together, freeing the syringe plunger for forward movement by removing the dosage gage from the path of the plunger, injecting into the right-hand bottle an amount of air equal to the required dosage of right-hand bottle ingredients by pushing the plunger forwardly as far as it will go, loading the syringe with slightly more right-hand bottle ingredients than required by pulling the plunger rearwardly until the plunger bottom flange clears the dosage gage, moving the dosage gage across the plunger to block the forward path of the plunger bottom flange, obtaining the correct dosage of right-hand bottle ingredients by injecting back into the right-hand bottle the overdosage amount of right-hand bottle ingredients by pushing the plunger bottom flange forwardly into contact with the dosage gage, withdrawing the needle from the right-hand bottle by moving the dosage gage and pulling the carriage away from the cradle, inserting the needle into the left-hand bottle by placing the syringe carriage into the left-hand alignment slot and moving the carriage and cradle together, loading the syringe with the correct dosage of the left-hand bottle ingredients by pulling the plunger back to the dosage stop indicator, and removing the needle from the left-hand bottle by moving the carriage and cradle apart, whereby the syringe has been loaded with the proper dosages of left and right-hand bottle ingredients.

* * * * *